United States Patent [19]

Dourdeville

[11] Patent Number: 5,637,208
[45] Date of Patent: Jun. 10, 1997

[54] SOLVENT PUMPING SYSTEM FOR CHROMATOGRAPHY WITH SWITCHING-VALVE

[76] Inventor: Theodore A. Dourdeville, 29 Bell Guzzle La., P.O. Box 400, Marion, Mass. 02738

[21] Appl. No.: 267,087

[22] Filed: Jun. 24, 1994

Related U.S. Application Data

[63] Continuation-in-part of Ser. No. 26,955, Mar. 5, 1993, abandoned.

[51] Int. Cl.$^6$ .............................. B01D 15/08; B01D 17/12
[52] U.S. Cl. .............................. 210/90; 96/106; 137/567; 210/101; 210/198.2; 417/2; 417/26; 417/44.2; 422/103
[58] Field of Search ..................... 210/90, 101, 198.2, 210/634, 656; 417/2–6, 26, 426, 38, 44.2, 519; 137/567; 96/105, 106; 422/103

[56] References Cited

U.S. PATENT DOCUMENTS

| | | | |
|---|---|---|---|
| 4,714,545 | 12/1987 | Bente et al. | 210/101 |
| 4,767,279 | 8/1988 | Dourdeville et al. | 210/198.2 |
| 5,253,981 | 10/1993 | Yang et al. | 417/3 |
| 5,308,583 | 5/1994 | Sanuki | 422/103 |
| 5,360,320 | 11/1994 | Jameson et al. | 417/5 |
| 5,393,434 | 2/1995 | Hutchins et al. | 210/101 |
| 5,457,626 | 10/1995 | Wolze | 210/198.2 |

*Primary Examiner*—Joseph W. Drodge
*Attorney, Agent, or Firm*—Huw R. Jones; Brian L. Michaelis

[57] ABSTRACT

A pumping system for continuously delivering fluid at a selected flow rate to a receiving system. The system includes at least a first and a second pumping unit, each of the individual units comprises a syringe and a valve. The syringe comprises a piston and a piston actuator, cylinder, and pressure sensor. The valve comprises a positively-actuated zero switching volume valve and valve actuator. The first and second pumping units are in fluid communication with one another and are capable of independent actuation. The individual valves are arranged to isolate either the first syringe or the second syringe, respectively, from the receiving system while at least one of the syringes remains in fluid communication with the receiving system whereby system pressure can be continuously monitored and the selected system flow rate maintained. A controller receives inputs from the first and second pressure sensors and activates in response to the inputs the first and second syringes individually, and also activates the first and second valves individually such that when fluid communication is established between the isolated syringe and the receiving system substantially no system flow error is produced. The pressure sensor is positioned within each pumping unit, permitting a pumping unit which has been refilled offline to perform compression of its cylinder contents without perturbation of the on-line process, and which further permits discrimination of the point in the compression cycle where compression has been completed and fluid delivery to the system will commence.

8 Claims, 3 Drawing Sheets

SOLVENT PUMPING SYSTEM FOR CHROMATOGRAPHY WITH SWITCHING-VALVE

RELATED APPLICATION

This is a continuation-in-part of application Ser. No. 08/026,955 filed on Mar. 5, 1993, now abandoned.

BACKGROUND

1. Field of the Invention

This invention relates generally to pumping systems, particularly systems used in liquid chromatography separations and analyses. Specifically this invention pertains to providing liquid chromatography systems with a solvent sourcing capability of high reliability and high precision, and with the ability to provide time-varying compositions of solvents with high fidelity to the user-requested values, with minimum delivery delay time and delay volume, even at flow rates at or below 1 microliter per minute.

2. Description of the Prior Art

The practice of high-performance liquid chromatography (HPLC) generally requires that the molecular species to be separated or analyzed be dissolved in a liquid (the mobile phase) and conveyed by that liquid through a stationary column bed which may comprise closely packed particles or a membrane or other matrix support termed the stationary phase. The stationary phase presents a large surface area which is in intimate contact with the mobile phase. Mixtures of analyte compounds, dissolved in the mobile phase, can be separated during passage through the column by processes of adsorption or retention, which act differentially on the various analyte species. The differential retention causes the analytes to elute from the column in both a time-resolved and volume-resolved manner. The eluting analytes will typically transit through an on-line detector, where quantitative and/or qualitative examination of the analytes will occur. Additionally, in preparative chromatography, the time- and volume-resolved samples may be collected as distinct fractions, and passed on to a subsequent process for further use.

The elution behavior of analyte molecules is a function of the characteristics of both the stationary and the mobile phase. To the extent that the properties of the stationary phase may remain substantially fixed throughout the analysis, variation in elution behavior is then predominantly the result of variation in the properties of the mobile phase. In the isocratic mode of chromatography, the solvent composition remains substantially constant as a function of time, and analytes in the sample will tend to elute when a prescribed mobile phase volume has transited the column. In the gradient mode of chromatography, the solvent composition is required to change as a function of time, tracking a user-defined profile; in this mode, analytes will elute in response to both the composition of solvent delivered, and to the overall or integrated volume of solvent delivered. It is further understood that the model presented above is a highly simplified one, and that there can be more complex modes, including multiple modes, of interaction between the analyte species and the stationary and mobile phases, causing behavior which deviates from this simple model.

In light of the above, the requirements imposed on HPLC solvent delivery systems are severe. HPLC pumps are typically required to deliver solvents at pressures which can range from several pounds per square inch to as much as 10,000 pounds per square inch. Across that range of delivery pressures, HPLC pumps are expected to output the mobile phase solvent at precisely controlled flow rates, in a smooth and uniform manner. In the case of gradient chromatography, or in the case of isocratic chromatography where a fixed solvent composition is blended in real time during the separation, there is the further requirement that mobile phase composition as well as flow rate be precisely and accurately controlled during delivery, despite the fact that system operating pressure may be changing very substantially during the separation, and that the compressibilities of the constituent mobile phase solvents may be quite different. Brownlee, in U.S. Pat. No. 4,347,131, teaches the use of a single syringe-type pump for each solvent composition where each syringe is of large enough volume (typically 10 to 40 milliliter internal volume) that an entire analysis can be conducted within one cylinder delivery. The entire volume is pressurized at once and maintained online for the duration of the separation, and multicomponent solvents are blended on the high-pressure or outlet side of two or more such pumps. The implementation disclosed in Brownlee suffers from the effects of differential hydraulic capacitance presented to the system at run time, as well as transient effects associated with the discontinuous or stop/start mode of operation of these syringes. The undesireable effects of hydraulic capacitance derive from the fact that, during gradient chromatography, as solvent composition changes, solvent viscosity typically changes as well. In order for the column flow rate to remain constant, the system operating pressure must change in response to the changing viscosity.

The different solvents used to produce gradient chromatography differ markedly in their compressibilities. When two or more large, captive volumes of liquids, having differing compressibilities, are subjected to a changing hydraulic pressure, they will compress or relax to differing extents. Brownlee does not disclose any means for assuring that the solvent volume sourced to the HPLC system under gradient conditions will accurately track with the syringe displacement; instead the system disclosed in Brownlee will be in error by the amount of compression or relaxation experienced in the respective captive liquid volumes. Moreover, there is no guarantee that the volume of liquid in the Brownlee syringe will be sufficient to carry out the separation.

Trisciani et. al. (U.S. Pat. No. 4,980,296) teaches the use of a "learning cycle" which determines hydraulic capacitance prior to run-time, and stores the data in a memory, to attempt to offset these effects in syringe pumps. The weakness of this approach is that a volume correction can only be performed "after the fact" in response to a change of system pressure, which means that in practice, the correction is always lagging the intended composition sent to the column.

The large errors associated with the compression or relaxation of large volumes of fluid can be minimized by the use of small volume syringe pumps that utilize multiple syringe strokes to deliver solvent through the course of a chromatographic separation. However, these pumps suffer from flow perturbations associated with the transition of fluid delivery from one syringe cycle to the next, that transition interval being termed the syringe or piston crossover.

Likuski et. al. (U.S. Pat. No. 4,919,595) teaches use of a single syringe having a high-speed refill cycle to minimize the period of no fluid delivery. Likuski et. al. employ the gradient of the internal pressure rise of the syringe to detect the onset of the next fluid delivery cycle. The controller subsequently over-delivers to approximately make up the flow deficit, and then returns the syringe speed to normal. While this approach minimizes the period of no fluid delivery from the syringe, and reduces the average flow rate error, significant system flow and pressure perturbations still result at crossover.

Barlow et. al. (U.S. Pat. No. 4,980,059) teach the use of a single motor to drive multiple syringe pumps with overlapping delivery strokes to avoid discontinuous flow. When a substantially constant delivery rate is being maintained by a single syringe, there is a significant increase in flow when an additional syringe begins its delivery. Barlow teaches reduction of the syringe drive velocity while an additional syringe is delivering. The control arrangement monitors the delivery pressure perturbation and advances or retards the instant of change of syringe drive velocity on the subsequent stroke. This still results in the system flow and pressure being perturbed prior to corrective response.

An emerging area of chromatographic separation and analysis is developing around the use of extremely narrow bore separation columns. Such columns have been termed capillary columns, that name deriving from the internal diameter of the separation column, which will typically be in the range of 0.005 millimeters to 0.500 millimeters internal diameter. Such columns may be packed with a particulate packing material, or, in the smallest diametral range, the column wall itself, or a coating applied to that wall, will be used as the stationary phase. Mobile phase flow rates for particulate-packed capillary columns having internal diameters of 0.025 millimeters to 0.500 millimeters can typically range from 1 nanoliter per minute to 10 or more microliters per minute. These figures represent an approximately thousand-fold reduction in flow rate (and therefore volume of the separation) from what is currently practiced on, for example, the 4 millimeter internal diameter columns widely commercially available at this time. HPLC systems designed around capillary columns have particular utility when the HPLC separation is to be coupled with a downstream process which does not readily tolerate large amounts of HPLC mobile phase. Examples of such processes are: (1) mass spectrometry, which requires that the sample reside in the gas phase at high vacuum conditions prior to mass analysis, (2) infra red spectroscopy, where organic solvents used for HPLC must be eliminated because they represent an interference to analyte detection in the infra red region of the electromagnetic spectrum, and (3) micro-fraction collection, which requires that the analyte be deposited in a small volume on a collection substrate, with minimum associated background contamination from the HPLC mobile phase.

Substantially the same requirements for precision and accuracy of solvent composition and flow rate delivery exist as for larger-scale chromatography, but the mechanisms for controlling the delivery must now function at one one-thousandth the volume scale. In particular, the non-idealities of a given implementation which could be dismissed at a much larger volumetric scale give rise to overwhelmingly large perturbations to a system of the scale of capillary HPLC. Heretofore the prior art has not adequately addressed the problems of continuous, smooth flow on a capillary system scale.

SUMMARY OF THE INVENTION

The invention is directed to a pumping system for continuously delivering fluid at a called-for flow rate to a receiving system comprising: at least a first and a second pumping unit, each of said individual units comprising a syringe means and a valve means, the syringe means comprising a piston and piston actuator, piston seal, cylinder, and pressure sensor, the valve means comprising a positively-actuated zero switching volume valve and valve actuator, the first and second pumping units being in fluid communication with one another and also being capable of independent actuation;

the individual valve means arranged to isolate either the first syringe means or the second syringe means, respectively, from the receiving system while at least one of the syringe means remains in fluid communication with the receiving system whereby system pressure can be continuously monitored and system flow rate maintained; and controller means for receiving inputs from the first and second pressure sensors and activating in response to the inputs the first and second syringe means individually, and also activating the first and second valve means individually such that when fluid communication is established between the isolated syringe means and the receiving system substantially no system flow error is produced.

An object of this invention is to overcome the above-illustrated limitations and problems by causing the solvent compression phase of HPLC pump delivery to be fully isolated from the solvent delivery phase, such that compression of the solvent from substantially atmospheric pressure to system operating pressure, or to a value which is a function of system operating pressure, does not introduce pressure or flow errors into the chromatographic process. The isolation of these phases of pump operation into an offline solvent compression and an online solvent delivery is achieved through the use of a multiple-piston pump with fully independent actuating means for each piston, and use of a pressure sensor within each syringe means which can monitor the compression process and indicate to the control means when system pressure (or a value which is a function thereof) has been precisely attained.

It is another object of this invention to avoid incurring volumetric errors in the chromatography process during the transition from the offline solvent compression phase to the online solvent delivery phase through the use of a cylinder valving means, the actuation of which does not vary the system volume.

It is yet another object of this invention to avoid incurring volumetric errors in the chromatography process due to pressure mismatch between the offline and the online cylinder at the time of crossover transition, arising from relative drift in the independent cylinder pressure sensor output values, through the use of an inter-calibration process during the interval when the two or more cylinder pressure sensors are in hydraulic continuity.

The objects are also met in a pumping system wherein the valving means provides that one of the pressure sensor means is always in fluid communication with the system during operation, and where there are means for positioning the valves and driving the syringes to provide information for diagnosing the hydraulic integrity of the pumping system and obtaining a quantitative measure of the compressibility of the cylinder contents while the called-for flow is maintained to the receiving system.

The objects are also met in a system wherein a controller means is arranged and constructed such that the off-line syringe pressure is constantly adjusted to equal the system pressure when the system pressure is changing, such that switching the syringe on-line produces substantially no system pressure variations or flow rate errors.

Other objects, features and advantages will be apparent from the following detailed description of the invention taken in conjunction with the claims and accompanying drawings.

DETAILED DESCRIPTION OF THE INVENTION

Figure 1:
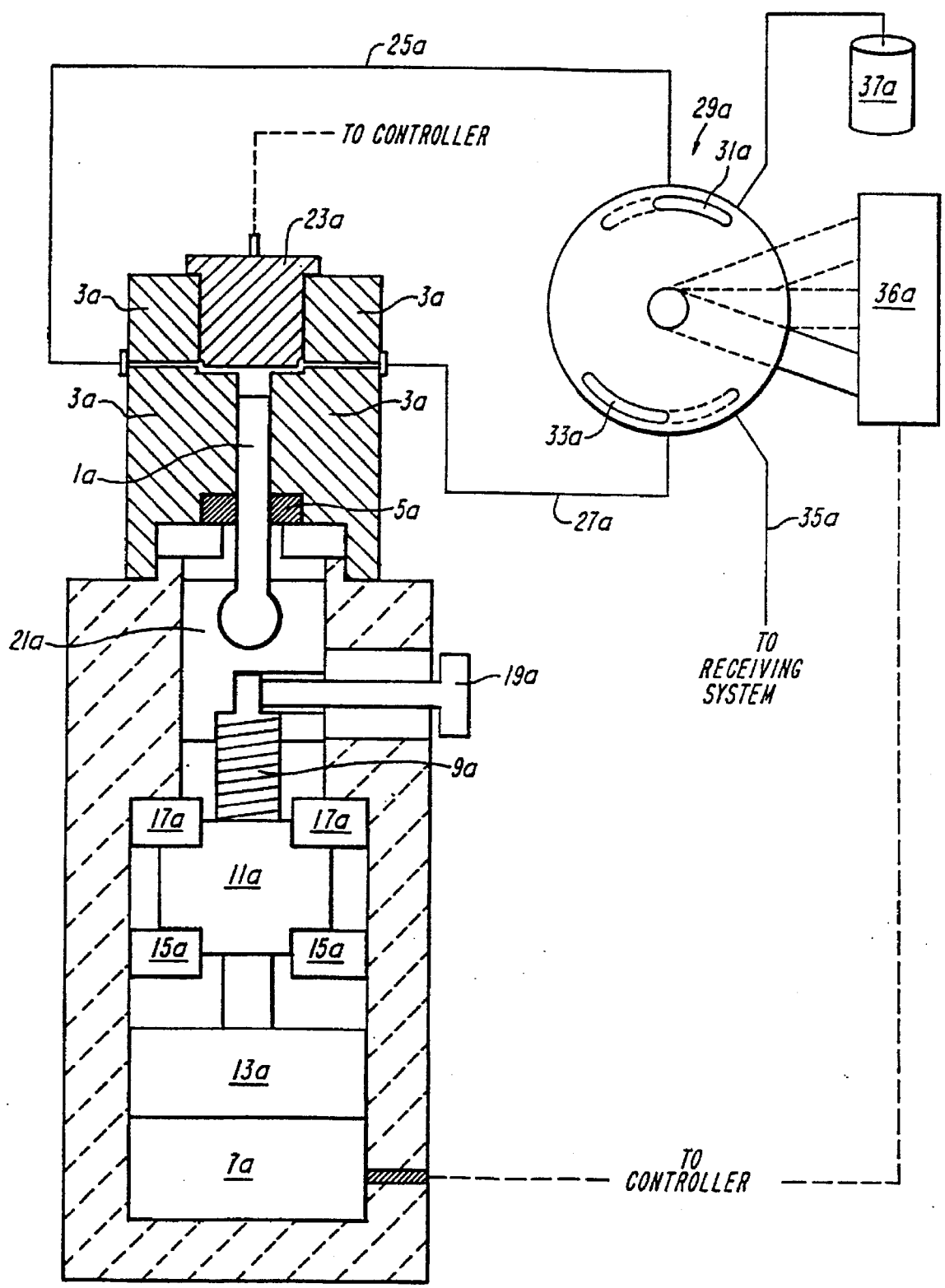
FIG. 1 is a block diagram of a single pumping unit, comprising a cylinder, piston, piston seal, piston actuator, valve, valve actuator, and pressure sensor.

FIG. 1 shows the arrangement of mechanical components which comprise one cylinder of a multiple-cylinder, continuous-delivery pumping system. The term "syringe" will be herein defined as a single cylinder with its associated piston, piston seal, piston actuator and pressure sensor. A syringe, with its associated valve means including valve and valve actuator, will constitute one pumping unit.

The pumping action of the unit is a positive displacement brought about by a piston 1a, the linear motion of which sweeps out a volume within the cylinder 3a. Hydraulic sealing between the piston and the cylinder is brought about by a self-energizing seal 5a, which resides in a cavity within the cylinder, and which interfaces with the outer diameter of the piston. The force to drive the piston is derived from a step motor 7a, the rotary motion of which is converted to linear motion by a lead-screw spindle 9a and nut 11 a arrangement. The step motor is optimally driven in microstep mode, and may include a reduction gear module 13a to further reduce the magnitude of the smallest increment piston motion attainable. The step motor rotates the nut, which is home by bearings 15a and 17a, which provide both radial and axial support to the nut, and thereby decouple the hydraulic forces, which are asserted axially onto the lead-screw and nut, from the step motor. The lead screw is free to move axially through a defined range, but is prevented from rotating by an anti-rotation element 19a, such technique being commonly known to those skilled in the art. The lead screw couples to the piston by means of a linear bearing 21a, which transfers the axial force while maintaining relatively precise axial alignment of the driven end of the piston.

At the opposing end of the cylinder is located a pressure sensor 23a, such as the Model 80-5000S from IC Sensors, Milpitas, CA. The cylinder is further provided with ports to which high-pressure tubing connections 25a, 27a can be made, which couple the cylinder to the valve assembly. The valve means 29a shown diagrammatically in FIG. 1 is of the type known as a positively actuated rotary spool valve, and preferably incorporates two hydraulically distinct flow channels 31a, 33a fabricated on a common rotor. Valves exemplifying this configuration are commercially available from Valco, Inc. (Houston, Tex.). An equivalent positively actuated valve means can be fabricated as a rotary face-seal valve, examples of which are commercially available from Rheodyne Corporation (Cotati, Calif.). In either case, the commutating parts of the fluid circuit are always in hydraulic continuity with the pump cylinder, and are therefore always maintained at cylinder pressure. An additional feature of both the rotary spool and rotary face-seal valve designs is that upon actuation, there is substantially no displacement of fluid into or out of the receiving system or the syringe resulting from commutation of the valve rotor. This zero-switching-volume behavior provides disturbance-free transitions during piston crossover. It is also a characteristic of these types of valves that extremely low leakage rates can be attained relative to the more conventional ball-and-seat check valves used in many chromatography pumps. The low leakage characteristic makes the use of such valves preferable for capillary scale HPLC. The valve rotor is actively driven by the pump controller and valve actuator to assume any one of three positions. In the following discussion of system operation, the nomenclature used for the three valve positions or states is: FILL, NC (to indicate no connection, equivalent to dead-ended), and DELIVER. In the FILL state, the flow channels on the valve rotor permit the pump cylinder to access a solvent reservoir 37a exclusively, with the fluid path to the system being blocked. In the DELIVER state, the flow channels provide hydraulic continuity from the cylinder to the system port 35a exclusively, with the channel to the reservoir being blocked. In the NC state, the fluid connections to both the reservoir and the system port are fully blocked. The use of a valve with two distinct commutating flow paths, and the use of two independent high-pressure tubing connections from the valve body into the cylinder, facilitates efficient flushing of the cylinder during solvent changeover. A rotary spool valve or rotary face seal valve incorporating only a single commutating fluid path to alternately connect a single syringe cylinder port to the solvent reservoir or to the system port can also be used, at the expense of reduced efficiency in flushing.

The valve actuator (ref. 36a.) typically employs either an electric motor with suitable gearing, capable of reversible actuation, or a double-acting pneumatic cylinder acting upon a bellcrank to provide the torque required to move the valve rotor through its angular range. The angular range is typically delimited by mechanical end-stops, with the FILL and DELIVER positions corresponding to the two extremes of travel. Either actuation mechanism can employ rotor position sensing, such that valve rotor motion can be arrested approximately midway between the FILL and DELIVER positions, such that the valve state termed NC (no connection) is produced. Other designs for valve actuators are well within the skill of one of ordinary skill in the art.

The system port 35a connects with one or more system ports from other, substantially identical pump units, to produce the continuous-delivery behavior described below.

Figure 2:
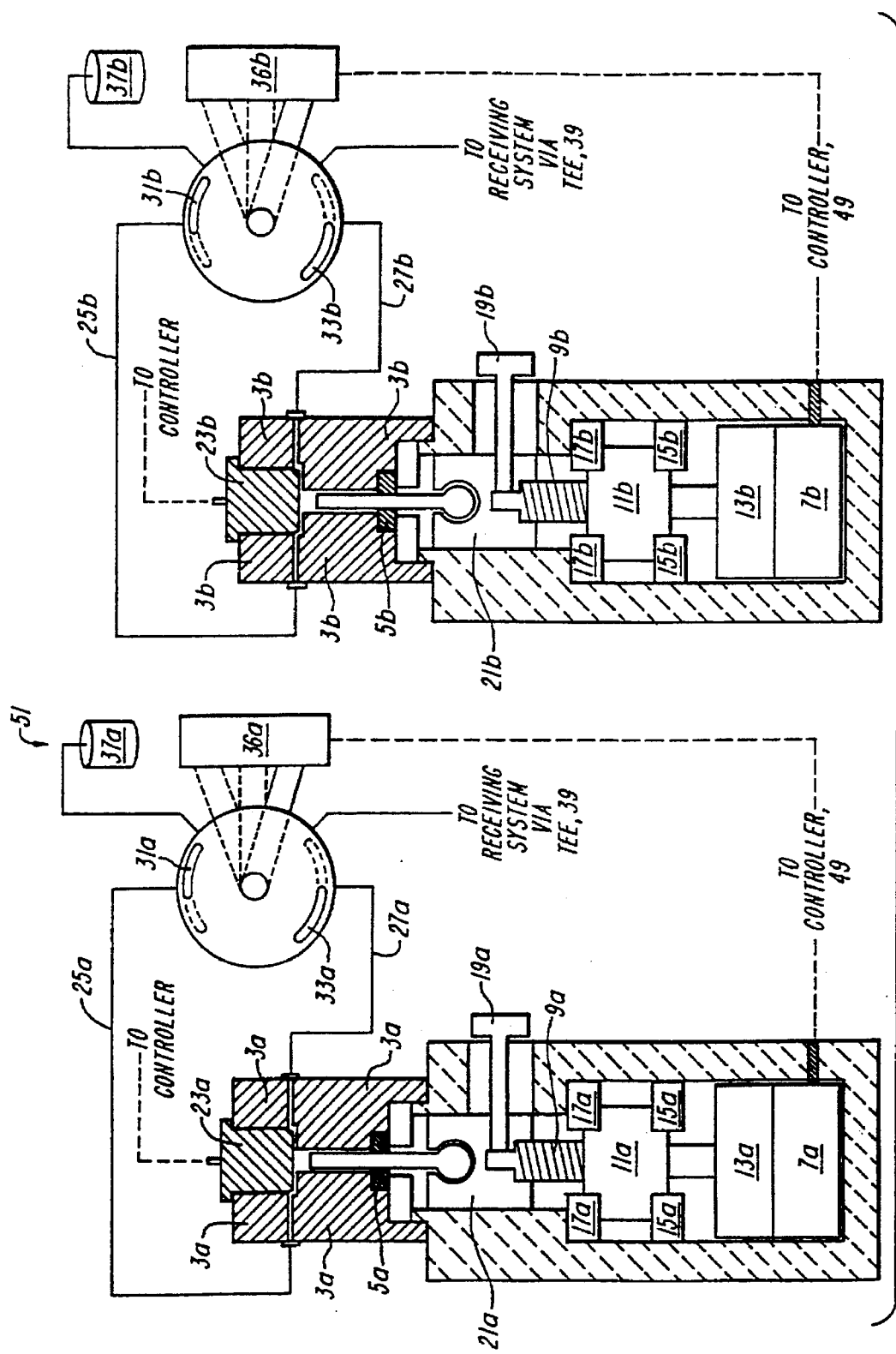
FIG. 2 is a block diagram of a continuous-delivery system comprising two pumping units of the type portrayed in FIG. 1.

FIG. 2 shows an arrangement of two substantiality identical pumping units, configured such that both pumping units draw fluid from the same reservoir 37a, and such that both units source fluid to a liquid chromatograph by means of a common connecting tee 39. The pumping units are shown under control from the common controller 49. The controller comprises a microprocessor-based subsystem built around a Motorola MC68000 processor which controls for each pumping unit the valve state, the rotation direction and step rate of the step motor, and maintains knowledge of the current position of the piston with respect to a defined reference position by means of digital counter hardware associated with the motor step state sequencing circuitry, and optionally a hardware position sensor. The implementation of each of these functions is well known to those skilled in the art. The controller is required to sequence the individual units through a series of basic actions summarized in TABLE 1, which represents the states of operation of the pumping system. The initiation or completion of basic actions by the constituent pumping units permits the controller to sequence through the state table to produce the continuous system output flow. In TABLE 1, the sign convention established is that positive piston velocities compress the cylinder contents and/or deliver the cylinder contents to the receiving system. Negative piston velocities decompress the cylinder contents and/or extract fluid from the system. In the comment column of the table, (L) and (R) are used to denote LEFT and RIGHT respectively. The term ARMED is used to denote a cylinder with fluid contents already compressed to the necessary pressure such that fluid delivery to the receiving system may commence upon control input from the pumping system controller with no further piston motion lost to compression of fluid.

With reference to TABLE 1, the text following details the operation of the continuous-delivery system; in this example, observation of the system operation commences at state 0, with delivery to system being sustained by the LEFT piston. The RIGHT piston is at rest, or zero velocity, having just completed its delivery. The RIGHT valve is sent to FILL position by the controller, producing state 1. A step frequency is applied to the RIGHT step motor, producing a non-zero piston velocity, of negative sign, filling the cylinder with fluid from the reservoir. When the controller, by means of digital counters tracking the step count applied to the motor, detects that the RIGHT piston is at end of stroke, it sets RIGHT piston velocity to zero, producing state 3. The controller then signals the RIGHT valve to transition to NC, to initiate the solvent precompression sequence, producing state 4. A step frequency is applied to the RIGHT step motor to produce a non-zero RIGHT piston velocity in the positive direction, compressing the cylinder contents (state 5).

Still referring to TABLE 1, when the pressure sensor internal to the RIGHT cylinder indicates a pressure equivalent to system pressure, the controller sets the RIGHT piston velocity to zero (state 6). The controller may hold the RIGHT cylinder at a fixed pressure above or below system pressure for an equilibration period, or, alternatively, system pressure may increase or decrease to a new value while the off-line RIGHT cylinder pressure is static. In either instance, there can be one or more fine equilibration steps taken by circulating between states 4 →5→6→5a43 4, where state 5a is essentially equivalent to state 5, differing only in that it achieves decompression of the cylinder contents by means of a negative velocity applied to the piston. The controller may optionally execute diagnostic routines on the RIGHT cylinder while traversing between states 4 and 6, for the purpose of assessing the presence or absence of solvent in the cylinder, the compressibility of that solvent, or the hydraulic integrity of the cylinder, all while maintaining the called-for flow to the receiving system.

Still referring to TABLE 1, when the system controller detects that the required degree of pressure matching between the offline and online cylinders has been accomplished, it can then dictate a transition for the RIGHT valve from NC to DELIVER, producing state 7. While in state 7, the controller can also dictate that an intercalibration take place between the RIGHT and LEFT pressure sensors, as both are viewing the same hydraulic circuit at this point. On command from the controller, a hand-off takes place between the currently delivering LEFT piston and and currently static RIGHT piston. The step frequency applied to the LEFT piston is ramped to zero while the step frequency applied to the RIGHT piston is ramped to the delivery flow rate in a precisely complementary fashion, such that the net flow to the system is unchanged, and state 8 is attained. Given that the LEFT and RIGHT pumping units are substantially identical, it will be noted that state 8 is the symmetrical state to state 0, differing only in that the RIGHT piston is the delivery piston, whereas in state 0 the LEFT piston is the delivery piston. An alternate way of viewing this relationship is that states 8 through 15 map directly over states 0 through 7, simply by cross-substitution of the words RIGHT and LEFT wherever they appear in the table. From state 15, the normal system operation which sustains constant fluid delivery entails transitioning to state 0, and repeatedly traversing the state table as described above. The transitions between states 7 and 8, and between states 15 and 0, characterize the intervals termed "handing off." During each handoff interval, the LEFT and RIGHT cylinder pressure sensors are in fluid communication, affording an opportunity to intercalibrate their outputs at system pressure, while maintaining the called-for flow to the receiving system.

TABLE 1

| STATE NO. | VALVE POSITION (LEFT) | PISTON VELOCITY (LEFT) | VALVE POSITION (RIGHT) | PISTON VELOCITY (RIGHT) | COMMENT |
|---|---|---|---|---|---|
| 0 | DELIVER | POSITIVE | DELIVER | STOP | HANDING OFF |
| 1 | DELIVER | POSITIVE | FILL | STOP | (R) EMPTY |
| 2 | DELIVER | POSITIVE | FILL | NEGATIVE | FILLING (R) |
| 3 | DELIVER | POSITIVE | FILL | STOP | (R) FILLED |
| 4 | DELIVER | POSITIVE | NC | STOP | ISOLATE (R) |
| 5 | DELIVER | POSITIVE | NC | POSITIVE | COMPRESS(R) |
| 6 | DELIVER | POSITIVE | NC | STOP | (R) ARMED |
| 7 | DELIVER | POSITIVE | DELIVER | STOP | HANDING OFF |
| 8 | DELIVER | STOP | DELIVER | POSITIVE | HANDING OFF |
| 9 | FILL | STOP | DELIVER | POSITIVE | (L) EMPTY |
| 10 | FILL | NEGATIVE | DELIVER | POSITIVE | FILLING (L) |
| 11 | FILL | STOP | DELIVER | POSITIVE | (L) FILLED |
| 12 | NC | STOP | DELIVER | POSITIVE | ISOLATE (L) |
| 13 | NC | POSITIVE | DELIVER | POSITIVE | COMPRESS (L) |
| 14 | NC | STOP | DELIVER | POSITIVE | (L) ARMED |
| 15 | DELIVER | STOP | DELIVER | POSITIVE | HANDING OFF |

Figure 3:
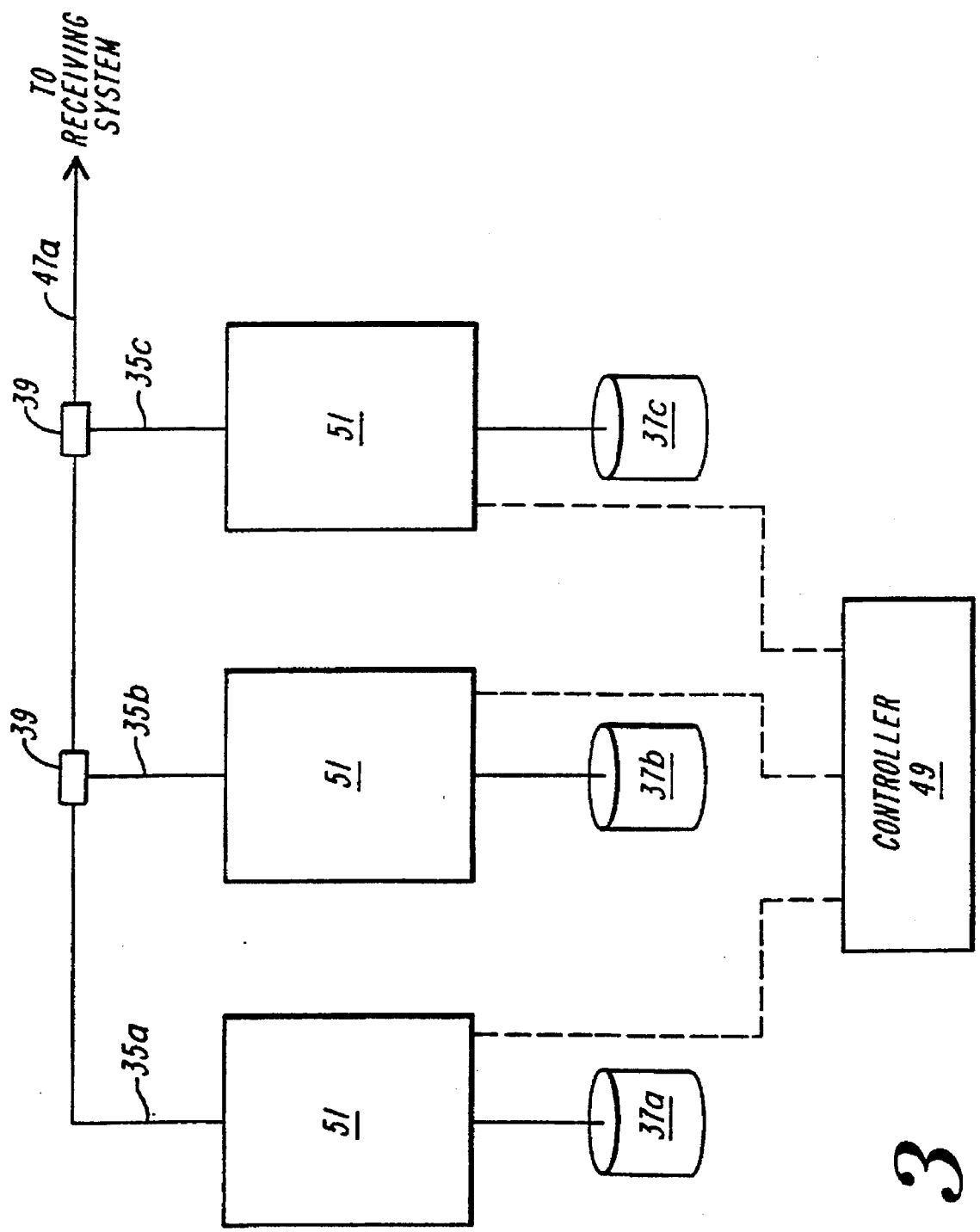
FIG. 3 is a block diagram showing multiple systems of the type portrayed in FIG. 2, connected in a manner suitable for use in high-pressure gradient liquid chromatography.

FIG. 3 depicts three continuous-delivery solvent pumping systems, each of which is configured as in FIG. 2. By carrying out the actions detailed in TABLE 1, each pumping system is capable of contributing one constituent of a mobile phase which is summed in the common output line 47a in order to produce gradient mode liquid chromatography. The pumping systems shown in this configuration are responsive to a single supervisory controller 49, one function of which is to establish the proportion of solvent composition to be delivered by each individual pumping system, by means of a flow rate setpoint passed to each. Because the fluid outputs of the individual pumping systems are smooth and continuous, a precise solvent composition is produced in the common output line which can eliminate the requirement to incorporate post-pump mixers to attenuate unwanted compositional fluctuations. Elimination of large post-pump mixing volumes is necessary to achieve the extremely low gradient response volumes required for capillary scale HPLC, and is desireable even for normal scale HPLC.

It will be apparent to those skilled in the art that the preferred embodiment described above may be configured to provide solvent delivery in a gradient system where solvent composition proportioning is performed on the low-pressure or inlet side of the pump, by means of a proportioning valve responsive to the system controller.

It will now be apparent to those skilled in the art that other embodiments, improvements, details and uses can be made consistent with the letter and spirit of the foregoing disclosure and within the scope of this patent, which is limited only by the following claims, construed in accordance with the patent law, including the doctrine of equivalents. An example is the use of this system for pumping supercritical fluids.

I claim:

1. A pumping system for delivering fluid from a solvent reservoir to a receiving system at a selected flow rate, comprising:

a pumping mechanism including a first pumping unit and a second pumping unit, said first pumping unit and said second pumping unit being arranged to continuously deliver said fluid from said solvent reservoir to said receiving system, each of said first pumping unit and said second pumping unit comprising, a syringe having an input port, an output port, and a cylinder, a piston dimensioned for actuation within said cylinder and a piston actuator in communication with said piston to effect actuation of said piston;

a positively-actuated zero switching volume valve and associated valve actuator selectively operable to enable fluid communication between said solvent reservoir and said input port, to enable fluid communication between said output port and said receiving system, and to isolate said syringe; and a fluid pressure sensor positioned to be in direct fluid communication with said cylinder, enabling continuous monitoring of cylinder pressure, said fluid pressure sensor providing an electrical output signal indicative of cylinder pressure independent of said positively-actuated zero switching volume valve state; and a controller operable for receiving said electrical output signals indicative of cylinder pressure from said fluid pressure sensor of said first pumping unit and from said fluid pressure sensor of said second pumping unit, responsive to control one of said first pumping unit and said second pumping unit as a delivery pumping unit to maintain said selected flow rate to said receiving system and to control the other of said first pumping unit and said second pumping unit to be off-line as an isolated pumping unit being re-filled, and to coordinate establishment of fluid communication between said isolated pumping unit after being refilled and said receiving system and isolation of said delivery pumping unit after delivery, in a manner which substantially avoids system flow error.

2. The pumping system of claim 1 wherein, for each pumping unit the positively-actuated zero switching volume valve is a positively actuated rotary spool valve.

3. The pumping system of claim 1 wherein, for each pumping unit, said positively-actuated zero switching volume valve further includes a no-connection position in which said piston is used to set pressure within said syringe while said syringe is isolated from said receiving system.

4. The pumping system of claim 1 wherein said receiving system is a liquid chromatograph.

5. The pumping system of claim 1 wherein said receiving system is a supercritical fluid chromatograph.

6. The pumping system of claim 1 wherein said pressure sensor associated with said isolated pumping unit is used to indicate hydraulic integrity of said isolated pumping unit while fluid delivery is maintained to the receiving system at the selected flow rate by the delivery pumping unit.

7. The pumping system of claim 1 wherein said pressure sensor associated with said isolated pumping unit is used to indicate compressibility of fluid contained within said isolated pumping unit, while fluid delivery is maintained to the receiving system at the selected flow rate by the delivery pumping unit.

8. A gradient chromatography system comprising at least two pumping systems configured according to claim 1 for delivering fluid to a common output line in order to produce a fluid composition gradient, comprising a supervisory controller in electrical communication with the at least two pumping systems whereby the supervisory controller establishes the proportion of solvent composition to be delivered by each individual pumping system to the common output line.

* * * * *